United States Patent [19]

Kulessa et al.

[11] 4,047,525

[45] Sept. 13, 1977

[54] INHALATOR FOR AGGLOMERATABLE PULVERULENT SOLIDS

[75] Inventors: Gerhard Kulessa, Stollberg; Elmar Mommertz, Laurentsberg near Aachen, both of Germany

[73] Assignee: Schering Aktiengesellschaft, Berlin & Bergkamen, Germany

[21] Appl. No.: 648,680

[22] Filed: Jan. 13, 1976

[30] Foreign Application Priority Data

Jan. 17, 1975 Germany ............................ 2502251

[51] Int. Cl.[2] ............................................ A61M 15/00

[52] U.S. Cl. .................................... 128/208; 128/266; 128/206

[58] Field of Search ................................ 128/195-210, 128/266; 222/189; 141/59

[56] References Cited

U.S. PATENT DOCUMENTS

| | | | |
|---|---|---|---|
| 881,988 | 3/1908 | Wirthlin ............................... | 222/189 |
| 2,587,215 | 2/1952 | Priestly ............................... | 128/208 |

*Primary Examiner*—Robert W. Michell
*Assistant Examiner*—Henry J. Recla
*Attorney, Agent, or Firm*—Millen & White

[57] ABSTRACT

For the inhalation of agglomeratable pulverulent medicaments and the like, there is disclosed a multi-chamber inhalator containing a storage chamber having an agglomerate comminutor and a porous distributor plate at one end (about 5-100 micron pore size) so that only desired particle size powder may pass through; an atomization chamber having a porous retention screen (the mesh being smaller than that of the distributor plate) for receiving the desired particle size powder; and a mouthpiece for inhaling powder from the atomization chamber.

19 Claims, 1 Drawing Figure

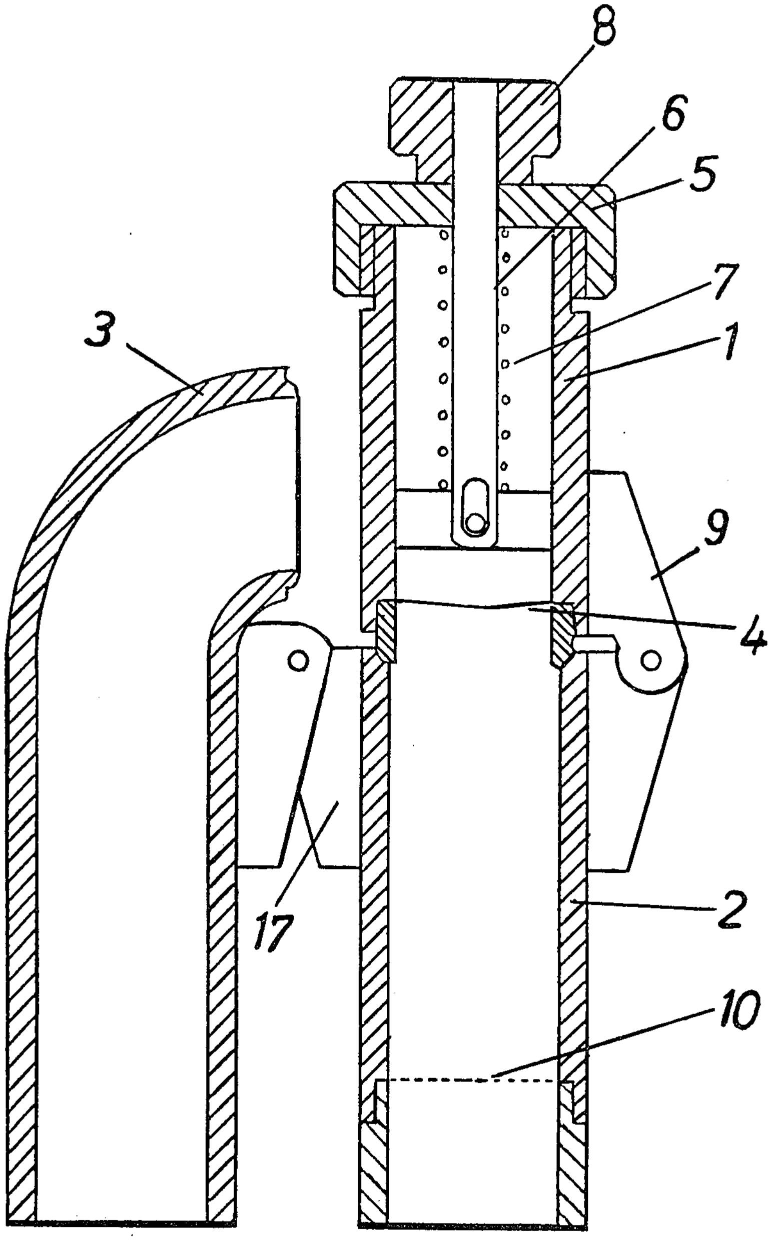
8
6
5
7
3
1
9
4
17
2
10

INHALATOR FOR AGGLOMERATABLE PULVERULENT SOLIDS

BACKGROUND OF THE INVENTION

This invention relates to an apparatus and method for the inhalation of pulverulent solids.

It is known that powdery medicinal substances and diagnostic agents are utilized for the treatment of diseases of the respiratory tract and for the diagnosis thereof.

For administering these powdery medicinal substances and diagnostic agents, inhalators have been developed (e.g., Belgian Pat. No. 804,645 and U.S. Pat. No. 3,795,244). However, it is not uncommon for certain powdery materials to agglomerate during storage, and when this phenomena occurs, the conventional inhalators are relatively useless.

SUMMARY

An object of the present invention is to provide an improved apparatus and method for the inhalation of pulverulent solids so as to solve the problem associated with agglomerated pulverulent medicinal substances and diagnostic agents.

Upon further study of the specification and appended claims, further objects and advantages of this invention will become apparent to those skilled in the art.

To attain these objects, there is provided, in accordance with the apparatus aspect of the invention:

an inhalator suitable for the administration of agglomeratable pulverulent solids, said inhalator comprising:

a container for pulverulent solids sealed at one end, and means associated with the other end of said container for expelling powder of a predetermined maximum particle size from said container, said means including a porous distributor plate;

an atomizing chamber open at one end and adapted for communication with said container for receiving said powder expelled through said porous distributor plate, said atomizing chamber containing at the other end thereof a porous retention plate, the pores of said retention plate being sufficiently smaller than the pores of said porous distributor plate so as to retain said expelled pulverulent solids in said atomizing chamber.

In this way, the atomizing chamber is filled only with powdery solids having a defined particle size optimal purposes of inhalation, these solids being thereafter atomized during inhalation in an optimum manner.

The distributing plate preferably has a mesh size of 5–100 $\mu$, and the retaining plate preferably has a mesh width which is ½ to 1/50 the size of that of the distributing plate.

For practical purposes, the volume of the container is generally about 1 to 100 ml. and the volume of the atomizing chamber about 5 to 100 ml.

Any convenient mouthpiece can be used for purposes of inhalation. For example, the mouthpiece could be formed as a unit with the atomizing chamber, as a stoppered radially extending tube, i.e. a T joint. It is preferred, however, that the mouthpiece be a separate piece having one end adaptable for insertion into an oral cavity and the other end adapted for communication with the open end of the atomizing chamber.

It is also a preferred embodiment of this invention to provide a comminutor (any device that comminutes) in the container so as to permit the expeditious size-reduction of agglomerated pulverulent solids. A variety of techniques can be used for this purpose, e.g., as simple as a dense ball incorporated within the container. A particularly preferred embodiment embraces the use of an agitator driven manually by an axle extending through the sealed end of the container. The axle is preferably spring biased against the distributing plate but is also axially movable.

In the device of this invention, the container, the atomizing chamber and the mouthpiece are preferably made of a synthetic resin, glass, or metal and are preferably of a tubular shape. The components can be associated as separate parts in a kit or in a hinged assembly and connected with each other only when the device is used. Alternatively, the apparatus can be designed as a unified structure whereby the pieces are joined to one another in the configuration of a T or a Y.

In the method aspect of the invention, the apparatus is particularly useful in administering for example the following pulverulent solids: medical inhalants or diagnostic solids which are agglomerable because of their hygroscopic or electrostatic nature.

BRIEF DESCRIPTION OF THE DRAWING

The appended drawing is a verticle sectional view of the preferred embodiment of the apparatus.

DETAILED DESCRIPTION OF THE DRAWING

The apparatus comprises a tubular container 1 for the accomodation of the pulverulent solids, a tubular atomizing chamber 2, and a tubular mouthpiece 3, each of which have the same internal and external diameters. The tubular container 1 is provided with a distributor plate 4 consisting of stainless steel mesh having a pore diameter of 20 microns, a sealing cap 5, and an agitator 6 extending through the sealing cap for comminuting aggregates, thereby facilitating the delivery of powder through the plate. The agitator is biased against the distributor plate 4 by means of a spring 7 and carries a button-like flared portion 8 above the sealing cap. The container 1 is connected to the atomizing chamber 2 by a hinge 9.

The agitator has two blades which are connected to a horizontal disk so that the agitator would resemble a piston.

The atomizing chamber 2 has a retention plate 10 consisting of stainless steel mesh having a pore diameter of 10 $\mu$ and is joined to the mouthpiece 3 by a second hinge 17.

When not being used, the various pieces are provided with appropriate conventional stoppers (not shown) for sanitary reasons as well as to prevent leakage of the powder from the container.

In use, the container 1, charged with the pulverulent solids to be inhaled, is placed on the atomizing chamber 2, and the solids are introduced into the chamber by turning the agitator.

The container 1 is removed, the mouthpiece 3 is attached to the chamber, and the powder is inhaled by the patient.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. An inhalator suitable for the administration of agglomeratable pulverulent solids, said inhalator comprising:

a container having a volume of about 1 to 100 ml for pulverulent solids and sealed at one end, and means associated with the other end of said container for expelling powder of a predetermined maximum particle size from said container, said means including a porous distributor plate having a pore size of 5–100 microns;

an atomizing chamber having a volume of about 5 to 100 ml, open at one end, said one end of said atomizing chamber being removably attached to said other end of said container for receiving said powder expelled through said porous distributor plate, said atomizing chamber containing at the other end thereof a porous retention plate, the pores of said retention plate being sufficiently smaller than the pores of said porous distributor plate so as to retain said expelled pulverulent solids in said atomizing chamber; and means for communicating said atomizing chamber with an oral cavity of a recipient.

2. An inhalator according to claim 1, said means for communicating said atomizing chamber with an oral cavity comprising a tubular mouthpiece having one end thereof adaptable for insertion into an oral cavity and the other end adapted for communication with said atomizing chamber.

3. An inhalator according to claim 2 further comprising means for hingedly attaching said container to said atomizing chamber and for hingedly attaching said mouthpiece to said atomizing chamber.

4. An inhalator according to claim 1 further comprising means for hingedly attaching said container to said atomizing chamber.

5. An inhalator according to claim 1, said means for expelling said powder further including a comminutor for agglomerated pulverulent solids.

6. An inhalator according to claim 5, said comminutor being a spring biased agitator having a rotatable and vertically movable axis.

7. An inhalator according to claim 1, said retention plate having pore diameters of about ½ to 1/50 of the pores of the distributor plate.

8. An inhalator according to claim 7, said means for expelling said powder further including a comminutor for agglomerated pulverulent solids.

9. An inhalator according to claim 1, wherein said means for communicating said atomizing chamber with an oral cavity of a recipient comprises an opening is said atomizing chamber.

10. A method of administering an agglomerated pulverulent solid, said method comprising storing an agglomeratable pulverulent solid in a small container sealed at one end and provided with a comminutor and a porous distributor plate; comminuting said pulverulent solids and expelling resultant powder through the porous distributor plate into an atomizing chamber having a porous retention plate, the pores of the retention plate being sufficiently small so as to retain said expelled powder; and inhaling resultant powder from said atomizing chamber.

11. An inhalator kit suitable for the administration of agglomeratable pulverulent solids, said inhalator kit comprising:

a container foor pulverulent solids seals at one end, and means associated with the other end of said container for expelling powder of a predetermined maximum particle size from said container, said means including a porous distributor plate;

an atomizing chamber open at one end, said one end of said atomizing chamber being removably attached to said other end of said container for receiving said powder expelled through said porous distributor plate, said atomizing chamber containing at the other end thereof a porous retention plate. The pores of said retention plate being sufficiently smaller than the pores of said porous distributor plate so as to retain said expelled pulverulent solids in said atomizing chamber; and means for communicating said atomizing chamber with an oral cavity of a recipient.

12. An inhalator according to claim 11, said means for communicating said atomizing chamber with an oral cavity comprising a tubular mouthpiece having one end thereof adaptable for insertion into an oral cavity and the other end adapted for communication with said atomizing chamber.

13. An inhalator according to claim 11 wherein said means for communicating said atomizing chamber with an oral cavity of a recipient comprises an opening in said atomizing chamber.

14. An inhalator suitable for the administration of agglomeratable pulverulent solids, said inhalator comprising:

a container for pulverulent solids sealed at one end, and means associated with the other end of said container for expelling powder of a predetermined maximum particle size from said container, said means including a porous distribution plate;

an atomizing chamber open at one end, said one end of said atomizing chamber being removably attached to said other end of said container for receiving said powder expelled through said porous distributor plate, said atomizing chamber containing at the other end thereof a porous retention plate, the pores of said retention plate being sufficiently smaller than the pores of said porous distributor plate so as to retain said expelled pulverulent solids in said atomizing chamber;

means for hingedly attaching said container to said atomizing chamber; and means for communicating said atomizing chamber with an oral cavity of a recipient.

15. An inhalator according to claim 14, said means for communicating said atomizing chamber with an oral cavity comprising a tubular mouthpiece having one end thereof adaptable for insertion into an oral cavity and the other end adapted for communication with said atomizing chamber.

16. An inhalator according to claim 15 further comprising means for hingedly attaching said mouthpiece to said atomizing chamber.

17. An inhalator suitable for the administration of agglomeratable pulverulent solids, said inhalator comprising:

a container for pulverulent solids sealed at one end, and means associated with the other end of said container for expelling powder of a predetermined maximum particle size from said container, said means including a porous distributor plate, and a comminutor for breaking up agglomerated pulverulent solids;

an atomizing chamber open at one end, said one end of said atomizing chamber being removably attached to said other end of said container for receiving said powder expelled through said porous distributor plate, said atomizing chamber containing at the other end thereof a porous retention plate, the pores of said retention plate being sufficiently smaller than the pores of said porous distributor plate so as to retain said expelled pulverulent solids in said atomizing chamber; and means for communicating said atomizing chamber with an oral cavity of a recipient.

18. An inhalator according to claim 17, said comminutor being a spring biased agitator having a rotatable and vertically movable axis.

19. An inhalator suitable for the administration of agglomeratable pulverulent solids, said inhalator comprising:

a container for pulverulent solids sealed at one end, and means associated with the other end of said container for expelling powder of a predetermined maximum particle size from said container, said means including a porous distributor plate having a pore size of 5-100 microns;

an atomizing chamber open at one end, said one end of said atomizing chamber being removably attached to said other end of said container for receiving said powder expelled through said porous distributor plate, said atomizing chamber containing at the other end thereof a porous retention plate, the pores of said retention plate having pore diameters of about ½ to 1/50 of the pores of the distributor plate, thereby being sufficiently smaller than the pores of said porous distributor plate so as to retain said expelled pulverulent solids in said atomizing chamber; and means for communicating said atomizing chamber with an oral cavity of a recipient.

* * * * *